-continued

|  | Test 1 | Test 2 |
| --- | --- | --- |
| Selectivities, wt. % | | |
| Aromatics | 71.3 | 76.9 |
| $C_4^+$ Nonaromatics | 2.5 | 6.5 |
| $C_1 + C_2$ | 22.9 | 11.6 |

The conversion results are similar for each catalyst. However, the selectivity of the dual catalyst system towards aromatic is significantly higher than that exhibited by the single ZSM-5 containing catalyst. Additionally, the dual catalyst system has one-half the selectivity towards the production of undesirable $C_1$ and $C_2$ components than the single catalyst system. This Example clearly illustrates the utility of the process of the present invention in improving the overall aromatic yield of a dehydrocyclodimerization process, in comparison to a dehydrocyclodimerization process utilizing a single ZSM-5 containing catalyst.

What is claimed is:

1. A process for the dehydrocyclodimerization of $C_2$–$C_6$ aliphatic hydrocarbons comprising passing a feed stream comprising a $C_2$–$C_6$ aliphatic hydrocarbon component into a reaction zone and contacting the $C_2$–$C_6$ aliphatic hydrocarbon comprising feed stream with two discrete catalysts wherein the first discrete catalyst comprises a ZSM-5 zeolite component, a phosphorus-containing alumina component, and a metal component selected from the elements of Groups IIB–IVB of the Periodic Table of the Elements and wherein the second discrete catalyst, which is free of said ZSM-5 zeolite component, comprises a catalytic component of lesser acidity than the ZSM-5 zeolite component of the first discrete catalyst, said catalytic component being selected from the group consisting of crystalline aluminosilicates, metal oxides, amorphous silica-alumina, and crystalline silica and wherein the second discrete catalyst also comprises a phosphorus-containing alumina component and wherein the reaction zone is maintained at hydrocarbon conversion conditions sufficient to produce a product containing aromatic compounds.

2. The process of claim 1 further characterized in that the Group IIB–IVB metal component is gallium.

3. The process of claim 2 further characterized in that the reaction zone contains two discrete catalysts in weight ratios of the first discrete catalyst to the second discrete catalyst ranging from 1:1 to 19:1.

4. The process of claim 3 further characterized in that the two discrete catalysts are uniformly mixed throughout the reaction zone.

5. The process of claim 3 further characterized in that the two discrete catalysts are located in a multiplicity of distinct single catalyst containing beds.

6. A process for the dehydrocyclodimerization of a $C_2$-$C_6$ aliphatic hydrocarbon comprising passing a feed stream comprising $C_2$–$C_6$ aliphatic hydrocarbon into a reaction zone and contacting the $C_2$–$C_6$ aliphatic hydrocarbon feed stream with a catalytic system comprising two discrete catalysts at a weight ratio of the first discrete catalyst to the second discrete catalyst of from 1:1 to 19:1 wherein the first discrete catalyst comprises a ZSM-5 aluminosilicate zeolite component, a phosphorus-containing alumina component, and from 0.1 to 10 wt.% of a gallium component and the second discrete catalyst comprises a catalytically active silicalite component, and a phosphorus-containing alumina component, all at hyudrocarbon conversion conditions sufficient to produce a product containing aromatic compounds and recovering said aromatic compounds.

7. The process of claim 6 further characterized in that the phosphorus-containing alumina is present in the first discrete catalyst and the second discrete catalyst in an amount between 20 and 60 percent by weight of the total catalytic composite, respectively.

8. The process of claim 7 further characterized in that the phosphorus to alumina ratio of the phosphorus-containing alumina is from 1:1 to 1:100.

9. The process of claim 8 further characterized in that the hydrocarbon conversion conditions range in temperature from about 400° C. to 600° C., in pressure from 2 to 10 atmospheres, and in liquid hourly space velocity from 0.5 to 2.0 hr$^{-1}$.

10. The process of claim 9 further characterized in that the two discrete catalysts are located in a multiplicity of distinct single catalyst containing beds.

11. The process of claim 9 further characterized in that the two discrete catalysts are uniformly mixed throughout the reaction zone.

12. The process of claim 10 further characterized in that the gallium is present in the first discrete catalyst and the second discrete catalyst in an an amount ranging from 0.1-5.0 percent by weight of the total catalytic composite.

13. The process of claim 11 further characterized in that the gallium is present in the first discrete catalyst and second discrete catalyst in an amount ranging from 0.1-5.0 percent by weight of the total catalytic composite.

* * * * *

United States Patent [19]

Lambert et al.

[11] Patent Number: 4,746,764

[45] Date of Patent: * May 24, 1988

[54] CATALYTIC PROCESS FOR THE CONVERSION OF HYDROCARBONS

[75] Inventors: Susan L. Lambert, Rolling Meadows; R. Joe Lawson, Palatine; Russell W. Johnson, Elmhurst, all of Ill.

[73] Assignee: UOP Inc., Des Plaines, Ill.

[ * ] Notice: The portion of the term of this patent subsequent to Mar. 24, 2004 has been disclaimed.

[21] Appl. No.: 939,337

[22] Filed: Dec. 8, 1986

Related U.S. Application Data

[60] Continuation-in-part of Ser. No. 871,976, Jun. 9, 1986, Pat. No. 4,652,689, which is a division of Ser. No. 734,308, May 15, 1985, Pat. No. 4,619,906, and a continuation-in-part of Ser. No. 668,102, Nov. 5, 1984, Pat. No. 4,623,632.

[51] Int. Cl.[4] .............................................. C07C 2/52
[52] U.S. Cl. ..................................... 585/419; 208/138
[58] Field of Search ......................... 208/138; 585/419

[56] References Cited

U.S. PATENT DOCUMENTS 4,652,689 3/1987 Lambert et al. .................... 585/415

Primary Examiner—Curtis R. Davis
Attorney, Agent, or Firm—Thomas K. McBride; John F. Spears, Jr.

[57] ABSTRACT

A novel dehydrocyclization process for the conversion of $C_6$-plus paraffins to their corresponding aromatics is presented. This process is characterized by a unique catalytic composite which contains a nonacidic L-zeolite, a Group VIII metal component and sufficient surface-deposited alkali metal to provide a surface-deposited alkali metal index of from about 40 to about 500. A further characterization is that the catalyst is prepared without subjecting the L-zeolite to a solution having a pH of greater than 9, and without appreciable loss of $SiO_2$ from the L-zeolite.

5 Claims, 1 Drawing Sheet

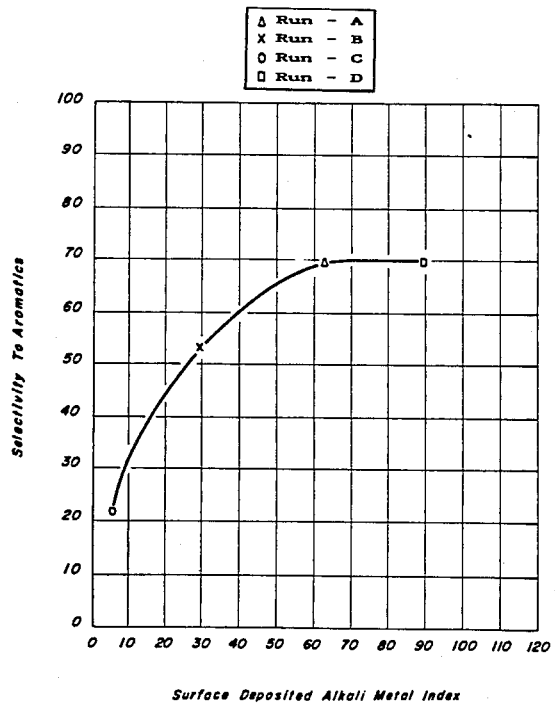

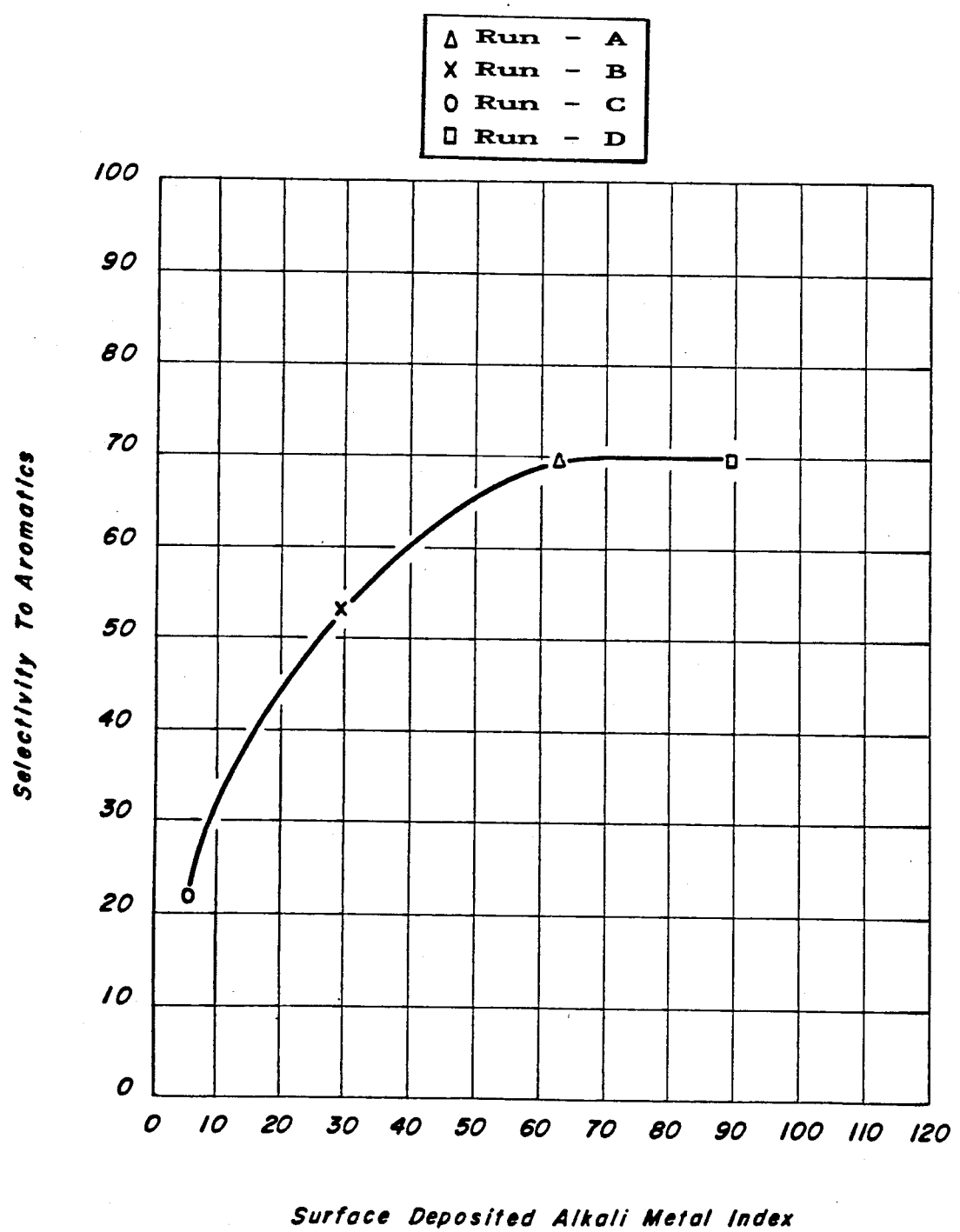

4,746,764

CATALYTIC PROCESS FOR THE CONVERSION OF HYDROCARBONS

CROSS-REFERENCE TO RELATED APPLICATIONS

This application is a continuation-in-part of prior copending application Ser. No. 871,976 filed June 9, 1986, now U.S. Pat. No. 4,652,689, which is a division of application Ser. No. 734,308 filed May 15, 1985, now U.S. Pat. No. 4,619,906, which is a continuation-in-part of copending application Ser. No. 668,102 filed Nov. 5, 1984, now U.S. Pat. No. 4,623,632 all of which are incorporated herein by reference.

BACKGROUND OF THE INVENTION

The present invention is directed toward a novel hydrocarbon conversion process, especially for effecting the dehydrocyclization of aliphatic hydrocarbons to aromatics. More particularly, the novel process enables the conversion of $C_6$-plus paraffins to their corresponding aromatics with a high degree of selectivity thereby enabling the facile production of large quantities of aromatics.

In the past, it has become the practice to effect conversion of aliphatic hydrocarbons to aromatics by means of the well-known catalytic reforming process. In catalytic reforming, a hydrocarbonaceous feedstock, typically a petroleum naphtha fraction, is contacted with a Group VIII-containing catalytic composite to produce a product reformate of increased aromatics content. The naphtha fraction is typically a full boiling range fraction having an initial boiling point of from about 10°–38° C. and an end boiling point of from about 107°–218° C. Such a full boiling range naphtha contains significant amounts of $C_6$-plus paraffinic hydrocarbons and $C_6$-plus naphthenic hydrocarbons. As is well known, these paraffinic and naphthenic hydrocarbons are converted to aromatics by means of multifarious reaction mechanisms. These mechanisms include dehydrogenation, dehydrocyclization, and isomerization followed by dehydrogenation. Accordingly, naphthenic hydrocarbons are converted to aromatics by dehydrogenation. Paraffinic hydrocarbons may be converted to the desired aromatics by dehydrocyclization and may also undergo isomerization. Accordingly then, it is apparent that the number of reactions taking place in a catalytic reforming zone are numerous and the typical reforming catalyst must be capable of effecting numerous reactions to be considered usable in a commercially feasible reaction system.

Because of the complexity and number of reaction mechanisms ongoing in catalytic reforming, it has become a recent practice to develop highly specific catalysts tailored to convert only specific reaction species to aromatics. Such catalysts offer advantages over the typical reforming catalyst which must be capable of taking part in numerous reaction mechanisms. Ongoing work has been directed toward producing a catalyst for the conversion of paraffinic hydrocarbons, particularly having six carbon atoms or more, to the corresponding aromatic hydrocarbon. Such a catalyst can be expected to be much more specific resulting in less undesirable side reactions such as hydrocracking. As can be appreciated by those of ordinary skill in the art, increased production of aromatics is desirable. The increased aromatic content of gasolines, a result of lead phase down, as well as demands in the petrochemical industry make $C_6$–$C_8$ aromatics highly desirable products. Accordingly, it would be most advantageous to have a process and a catalytic composition which is highly selective for the conversion of less valuable $C_6$-plus paraffins to the more valuable $C_6$-plus aromatics.

OBJECTS AND EMBODIMENTS

It is, therefore, a principal object of the present invention to provide a process utilizing a novel catalytic composition for the conversion of hydrocarbons. A more specific objective is to provide a process for the conversion of $C_6$-plus paraffinic hydrocarbons, especially $C_6$–$C_8$ paraffinic hydrocarbons, to their corresponding aromatics.

Accordingly, a broad embodiment of the present invention is directed toward a dehydrocyclization process characterized in that it comprises contacting at catalytic dehydrocyclization conditions a hydrocarbon charge stock with a catalytic composite comprising a nonacidic L-zeolite, a catalytically effective amount of a Group VIII metal component, and sufficient surface-deposited alkali metal to provide a surface-deposited alkali metal index of from about 40 to about 500, where the catalytic composite is prepared without subjecting the L-zeolite to a solution having a pH of greater than 9 and without appreciable loss of $SiO_2$ from the L-zeolite.

These as well as other objects and embodiments will become evident from the following, more detailed description of the present invention.

INFORMATION DISCLOSURE

Aluminosilicates containing alkali metals are well known in the art. For example, U.S. Pat. No. 3,013,986, issued Dec. 19, 1968, discloses an alkali metal loaded L-zeolite. In particular, this reference indicates that the potassium or the potassium/sodium form of the L-zeolite are the preferred starting materials for the alkali metal-loaded L-zeolite. The reference teaches that a dehydrated molecular sieve may be contacted with alkali metal vapors to produce an alkali metal-loaded molecular sieve wherein the alkali metal is contained within the interior of the zeolitic molecular sieve. The reference, however, does not disclose a nonacidic zeolite having composited therewith catalytically effective amounts of Group VIII metal component and surface-deposited alkali metal. Moreover, the reference does not disclose that such a composition would have any use as a hydrocarbon conversion catalyst.

U.S. Pat. No. 3,376,215, issued Apr. 2, 1968, discloses a hydrocarbon conversion catalyst comprising a cocatalytic solid support containing a Group VIII metal which support comprises (1) an adsorbent refractory inorganic oxide and (2) a mordenite structure zeolite having deposited thereon about 10 to about 1000 ppm by weight, based on zeolite, of a metal selected from the class of alkali metals, alkaline earth metals, and mixtures thereof. This reference teaches that the support comprising a mordenite form zeolite and a refractory oxide be cocatalytic. By way of contrast, an essential feature of the present invention is use of a nonacidic zeolite. In this nonacidic form, the zeolite of the present invention is not catalytic. Rather, the nonacidic zeolite acts to modify the catalytic Group VIII metal of the present invention. Accordingly, this reference does not disclose the novel catalyst of the present invention.

U.S. Pat. No. 3,755,486, issued Aug. 28, 1973, discloses a process for dehydrocyclizing $C_6$–$C_{10}$ hydrocarbons having at least a $C_6$ backbone using an Li, Na, or K zeolite X or Y or faujasite impregnated with 0.3 to 1.4% platinum. This reference, however, fails to disclose the advantages to be derived by utilizing a catalytic composite comprising a nonacidic zeolite having surface-deposited alkali metal. Likewise, U.S. Pat. No. 3,819,507, issued June 25, 1974, and U.S. Pat. No. 3,832,414, issued Aug. 27, 1974, while disclosing processes similar to that of U.S. Pat. No. 3,755,486, both fail to teach the use and advantages to be derived by such use of a nonacidic zeolite composited with platinum and surface-deposited alkali metal.

U.S. Pat. No. 4,140,320, issued Aug. 1, 1978, discloses a process for dehydrocyclizing aliphatic hydrocarbons utilizing a type L-zeolite having exchangeable cations of which at least 90% are alkali metal ions selected from the group consisting of ions of sodium, lithium, potassium, rubidium and cesium and containing at least one metal selected from the group which consists of metals of Group VIII, tin and germanium. This reference fails to disclose the catalytic composite of the present invention in that the alkali metal ions of the catalyst of this reference are all associated with ion exchange sites on the L-zeolite. There is no disclosure of an L-zeolite having surface-deposited alkali metal. U.S. Pat. No. 4,417,083, issued Nov. 22, 1983, discloses a process for dehydrocyclization utilizing a substantially nonacidic zeolite having a pore diameter larger than 6.5 angstroms and containing at least one metal selected from the group consisting of platinum, rhenium, iridium, tin, and germanium. Additionally, the catalyst contains sulfur and alkaline cations. However, in this reference, there is no disclosure of surface-deposited alkali metal. U.S. Pat. No. 4,416,806, issued Nov. 22, 1983, discloses yet another paraffin dehydrocyclization catalyst comprising platinum, rhenium as a carbonyl, and sulfur on a zeolitic crystalline aluminosilicate compensated in more than 90% by alkaline cations and having a pore diameter of more than 6.5 angstroms. This reference too, fails to disclose a catalytic composition for dehydrocyclization having surface-deposited alkali metal.

U.S. Pat. No. 4,430,200, issued Feb. 7, 1984, discloses a hydrocarbon conversion catalyst comprising a high silica zeolite such as mordenite or zeolite Y which has been base exchanged with an alkali metal. This reference too, however, fails to disclose a catalyst with surface-deposited alkali metal. Moreover, the reference merely discloses the use of the prior art catalyst in a cracking process and not a dehydrocyclization process.

U.S. Pat. No. 4,448,891, issued May 15, 1984, discloses a dehydrocyclization catalyst comprising an L-zeolite which has been soaked in an alkali solution having a pH of at least 11 for a time and at a temperature effective to increase the period of time over which the catalytic activity of the catalyst is maintained. Additionally, the catalyst contains a Group VIII metal. However, in the reference, the alkali soak is taught as modifying the silica content of the L-zeolite by reducing the $SiO_2$ content and altering the structure of the zeolite. After the alkali soak, the reference indicates that the L-zeolite is washed to remove excess ions. Accordingly, the catalyst of this reference does not have deposited thereon surface-deposited alkali metal. It, therefore, does not disclose the catalyst of the instant invention.

In summary then, the art has not recognized a dehydrocyclization process characterized in that it comprises contacting at catalytic dehydrocyclization conditions a hydrocarbon charge stock with a catalytic composite comprising a nonacidic L-zeolite, a catalytically effective amount of a Group VIII metal component, and sufficient surface-deposited alkali metal to provide a surface-deposited alkali metal index of from about 40 to about 500, where the catalytic composite is prepared without subjecting the L-zeolite to a solution having a pH of greater than 9 and without appreciable loss of $SiO_2$ from the L-zeolite. Moreover, the art has not recognized the attendant advantages to be derived from such a novel catalyst and use thereof.

DETAILED DESCRIPTION OF THE INVENTION

To reiterate briefly, the present invention relates to a dehydrocyclization process characterized in that it comprises contacting at catalytic dehydrocyclization conditions a hydrocarbon charge stock with a catalytic composite comprising a nonacidic L-zeolite, a catalytically effective amount of a Group VIII metal component, and sufficient surface-deposited alkali metal to provide a surface-deposited alkali metal index of from about 40 to about 500. Specifically, the catalytic composition is prepared without subjecting the L-zeolite to a solution pH of greater than 9 and without appreciable loss of $SiO_2$ from the zeolite. Moreover, the process of the invention has particular utility as a catalyst for the dehydrocyclization of $C_6$-plus paraffins, especially $C_6$–$C_{10}$ paraffins.

As heretofore indicated, it is an essential feature of the catalyst of the present invention that it comprise a nonacidic L-zeolite. By "nonacidic zeolite", it is to be understood that it is meant that the zeolite has substantially all of its cationic sites of exchange occupied by nonhydrogen cationic species. Preferably, such cationic species will comprise the alkali metal cations although other cationic species may be present. Irrespective of the actual cationic species present in the sites of exchange, the nonacidic zeolite in the present invention has substantially all of the cationic sites occupied by nonhydrogen cations, thereby rendering the zeolite substantially fully cationic exchanged. Many means are well known in the art for arriving at a substantially fully cationic exchanged zeolite and thus they need not be elaborated herein. The nonacidic zeolite of the present invention acts to modify the catalytic Group VIII metal and is substantially inert in the reaction. It is believed that the nonacidic zeolite of the present invention is noncatalytic and hence the requirement that it be nonacidic.

The especially preferred type of nonacidic zeolite of the present invention is L-zeolite. It is required that the cationic exchangeable sites of the L-zeolite be fully cationic exchanged with nonhydrogen cationic species. As also indicated above, typically the cations occupying the cationic exchangeable sites will comprise one or more of the alkali metals including lithium, sodium, potassium, rubidium, and cesium. An especially preferred nonacidic zeolite for application in the present invention is the potassium form of L-zeolite. It should also be understood, however, that the nonacidic L-zeolite of the invention may contain more than one type of the alkali metal cation at the cationic exchangeable sites, for example, sodium and potassium. As will be explained more fully hereinafter, this can occur as the result of competitive cationic exchanges which may take place during the deposition of the surface-deposited alkali metal. It is contemplated that the nonacidic L-zeolite may be intimately associated with a support matrix, however, the preferred formulation of the catalytic composite of the instant invention does not contain a support matrix. Thus, the catalytic composite comprises a non-matrix support nonacidic L-zeolite.

As is well known in the art, use of a support matrix enhances the physical strength of the catalyst. Additionally, use of a support matrix allows formation of shapes suitable for use in catalytic conversion processes. For example, the nonacidic zeolite of the present invention may be bound in the support matrix such that the final shape of the catalytic composite is a sphere. The use of spherical shaped catalyst is, of course, well known to be advantageous in various applications. In particular, when the catalyst of the instant invention is employed within a continuously moving bed hydrocarbon conversion process, a spherical shape enhances the ability of the catalyst to move easily through the reaction and regeneration zones. Of course, other shapes may be employed where advantageous. Accordingly, the catalytic composite may be formed into extrudates, saddles, etc.

The support matrix may comprise any support matrix typically utilized to bind zeolitic-containing catalytic composites. Such support matrices are well known in the art and include clays, bauxite, refractory inorganic oxides such as alumina, zirconium dioxide, hafnium oxide, beryllium oxide, vanadium oxide, cesium oxide, chromium oxide, zinc oxide, magnesia, thoria, boria, silica-magnesia, chromia-alumina, alumina-boria, etc. A preferred support matrix comprises silica, and an especially preferred support matrix comprises alumina. It is further preferred that the support matrix be substantially inert to the reactants to be converted by the composite as well as the other constituents of the composite. To this end, it is preferred that the support matrix be nonacidic to avoid promotion of undesirable side reactions. Such nonacidity may be induced by the presence of alkali metals such as those comprising the surface-deposited alkali metal.

If a support matrix is used to bind the nonacidic L-zeolite, the procedure for binding may be by any method known in the art. Such methods include pilling, extruding, granulating, marumarizing, etc. A particularly preferred method is the so-called oil-drop method.

Typically, in binding a zeolite in a support matrix by means of the oil-drop method, powdered zeolite is admixed with a sol comprising the desired support matrix or precursors thereof, and a gelling agent. Droplets of the resulting admixture are dispersed as spherical droplets in a suspending medium, typically oil. The gelling agent thereafter begins to cause gelation of the sol as a result of the change in the sol pH. The resulting gelled support matrix has bound therein the zeolite. The suspending medium helps maintain the spherical shape of the droplets. Useable suspending mediums include Nujol, kerosene, selected fractions of gas oil, etc. Many gelling agents are known in the art and include both acids and bases. Hexamethylenetetramine is only one such known gelling agent. The hexamethylenetetramine slowly decomposes to ammonia upon heating. This results in a gradual pH change and as a result, a gradual gelation.

Regardless of the exact method of binding the non-acidic L-zeolite in the support matrix, sufficient non-acidic L-zeolite may be used to result in a catalytic composite comprising from about 25 to about 75 wt.% nonacidic L-zeolite based on the weight of the zeolite and support matrix. The exact amount of nonacidic L-zeolite advantageously included in the catalytic composite will be a function of the support matrix and the specific application of the catalytic composite. A catalytic composite comprising about 50 to 75 wt.% potassium form of L-zeolite bound in alumina is advantageously used in the dehydrocyclization of $C_6-C_8$ nonaromatic hydrocarbons.

A further essential feature of the catalyst of the present invention is the presence of catalytically effective amounts of a Group VIII metal component, including catalytically effective amounts of nickel component, rhodium component, palladium component, iridium component, platinum component, or mixtures thereof. Especially preferred among the Group VIII metal components is a platinum component. The Group VIII metal component may be composited with the other constituents of the catalytic composite by any suitable means known in the art. For example, a platinum component may be impregnated by means of an appropriate solution such as a dilute chloroplatinic acid solution. Alternatively, the Group VIII metal component may be composited by means of ion exchange in which case, some of the cationic exchange sites of the nonacidic zeolite may contain Group VIII metal cations. After ion exchange, the Group VIII metal may be subject to a low temperature oxidation prior to any reduction step. The Group VIII metal component may be composited with the other constituents either prior to or subsequent to the deposition of the hereinafter described surface-deposited alkali metal. Additionally, the Group VIII metal may be composited with the nonacidic zeolite and thereafter, the nonacidic zeolite containing Group VIII metal may be bound with the support matrix.

Irrespective of the exact method of compositing the Group VIII metal component into the catalytic composite, any catalytically effective amount of Group VIII metal component may be employed. The optimum Group VIII metal component content will depend generally on which Group VIII metal component is utilized in the catalyst of the invention. However, generally from about 0.01 to about 5.0 wt.% of the Group VIII metal component based on the weight of the nonacidic L-zeolite, Group VIII metal component and surface-deposited alkali metal may be advantageously utilized.

It is believed that best results are achieved when the Group VIII metal is substantially all deposited on the nonacidic zeolite. It is also advantageous to have the Group VIII metal component highly dispersed. The Group VIII metal component is most effective in a reduced state. Any suitable means may be employed for reducing the Group VIII metal component and many are well known in the art. For example, after compositing, the Group VIII metal component may be subjected to contact with a suitable reducing agent, such as hydrogen, at an elevated temperature for a period of time.

In addition to comprising a Group VIII metal component, it is contemplated in the present invention that the catalyst thereof may contain other metal components well known to have catalyst modifying properties. Such metal components include rhenium, tin, cobalt, indium, gallium, lead, zinc, uranium, thallium, dysprosium, germanium, etc. Incorporation of such metal components have proven beneficial in catalytic reforming as promoters and/or extenders. Accordingly, it is within the scope of the present invention that catalytically effective amounts of such modifiers may be beneficially incorporated into the catalyst of the present invention improving its performance.

Irrespective of the particular Group VIII metal component or catalytic modifiers composited in the catalyst of the invention, the catalyst of the present invention also comprises sufficient surface-deposited alkali metal to provide a surface-deposited alkali metal index of at least 10 and preferably from about 40 to about 500. It is to be understood that by "surface-deposited alkali metal", it is meant that the alkali metal component is not associated with a cationic exchangeable site, but rather is excess alkali metal component above that amount required to occupy substantially all of the cationic exchangeable sites. It is to be further understood that the surface-deposited alkali metal index is indicative of the amount of such surface-deposited alkali metal. As used herein, the term "surface-deposited alkali metal index" is defined as $10^4$ multiplied by the moles per liter of soluble alkali metal yielded by the weight of catalytic composite comprising 0.5 g of nonacidic zeolite placed in 10 cc of deionized water as measured at 25° C. by an electrode sensitive to said alkali metal.

Any of the alkali metals may be used as the surface-deposited alkali-metal including lithium, sodium, potassium, rubidium, cesium, and mixtures thereof. Potassium on the potassium form of L-zeolite is especially preferred.

It should be understood that the surface-deposited alkali metal need not necessarily be the same alkali metal as the cations occupying the cationic exchangeable sites of the nonacidic L-zeolite. Hence, the surface-deposited alkali metal may, for example, comprise rubidium while the nonacidic zeolite may comprise the potassium form of L-zeolite. Likewise, the surface-deposited alkali metal may comprise more than one alkali metal. Accordingly, the surface-deposited alkali metal may, for example, comprise potassium and cesium on the potassium form of L-zeolite.

The surface-deposited alkali metal may be composited with the catalyst of the present invention by any suitable technique. Standard impregnation techniques may be employed utilizing an aqueous solution of an alkali metal salt. Either basic or neutral salts may be used. For example, when surface-depositing potassium on a catalyst comprising the potassium form of L-zeolite, the impregnation solution may comprise a basic salt of potassium such as $KHCO_3$, $K_2CO_3$, KOH, etc. Alternatively, a solution comprising neutral potassium salt such as KCl may be used.

As indicated, a basic alkali metal salt solution may be used to surface-deposit the alkali metal. However, it is a requirement of the present invention that the basicity of such an alkali metal salt solution not be so strong as to modify the zeolite structure. Preferably, the catalyst composite is prepared without subjecting the L-zeolite to a solution having a pH greater than 9. At pH values exceeding 9, silica has tendency to solubilize, thus lowering the $SiO_2/Al_2O_3$ molar ratio of the zeolite as $SiO_2$ is lost from the zeolite. Concomitant with the silica loss is a reduction of the purity of the L-zeolite as measured by X-ray diffraction analysis. Any appreciable loss of $SiO_2$ from the L-zeolite and/or loss of zeolite purity introduces uncertainty in the surface deposited alkali metal index measurement.

Therefore, another feature of the present invention is that the catalytic composite be prepared without appreciable loss of $SiO_2$ from the L-zeolite. What is meant by the term "appreciable" is a silica loss of greater than 0.05 wt.% of $SiO_2$ based on the weight of the L-zeolite, Group VIII metal component, and surface-deposited alkali metal.

Also associated with silica removal is an expansion in the $a_o$ lattice dimension as measured by X-ray diffraction analysis. Because of the requirement of not contacting the L-zeolite with solutions having a pH greater than 9, catalysts prepared in accordance with the instant invention do not exhibit either the lattice expansion or a decrease in the $SiO_2/Al_2O_3$ molar ratio.

It should further be noted that when it is desired to have a surface-deposited alkali metal different than the alkali metal cation associated with the cation exchangeable sites of the nonacidic L-zeolite, some amount of competitive ion exchange may take place during impregnation. For example, when surface-depositing rubidium on the potassium form of L-zeolite, a competitive ionic exchange may take place wherein some of the rubidium from the impregnation solution replaces some of the potassium on the cationic exchangeable sites of the nonacidic L-zeolite. In turn, this displaced potassium will be surface-deposited on the zeolite along with the balance of the rubidium. The net result is that the cations at the cationic exchangeable sites will comprise rubidium and potassium ions while the surface-deposited alkali metal will comprise rubidium and potassium. A catalyst having such a distribution is within the scope of the present invention, but may not give the best results. There are, however, techniques well known in the art of catalyst preparation to minimize the problem of competitive exchange and as a consequence, further elaboration thereof for one of ordinary skill in the art is unnecessary.

As heretofore indicated, the catalytic composite of the present invention has particular utility as a hydrocarbon conversion catalyst. Accordingly, a hydrocarbon charge stock is contacted at hydrocarbon conversion conditions with the catalytic composite of the present invention. A wide range of hydrocarbon conversion conditions may be employed and the exact conditions will depend upon the particular charge stock and reaction to be effected. Generally, these conditions include a temperature of about 260°–815° C., a pressure of from atmospheric to about 100 atmospheres, a liquid hourly space velocity (calculated on the basis of equivalent liquid volume of the charge stock contacted with the catalyst per hour divided by the volume of conversion zone containing catalyst) of about 0.2 to 15 $hr^{-1}$. Furthermore, hydrocarbon conversion conditions may include the presence of a diluent such as hydrogen. When such is the case, the hydrogen to hydrocarbon mole ratio may be from about 0.5:1 to about 30:1.

As heretofore indicated, the instant invention involves the process of converting a hydrocarbon charge stock at catalytic dehydrocyclization conditions. In particular, the preferred hydrocarbon charge stock comprises $C_6$–$C_8$ nonaromatic hydrocarbons. Accordingly, the present invention involves contacting a hydrocarbon charge stock comprising $C_6$–$C_8$ nonaromatic hydrocarbons with the catalyst described hereinabove at dehydrocyclization conditions. Dehydrocyclization conditions include a pressure of from about 0 to about 1000 psig, with the preferred pressure being from about 25 to about 600 psig, a temperature of from about 427°–650° C., and a liquid hourly space velocity of from about 0.1 to about 10 $hr^{-1}$. Preferably, hydrogen may be employed as a diluent. When present, hydrogen may be circulated at a rate of from about 1 to about 10 moles of hydrogen per mole of charge stock hydrocarbon.

In accordance with the present invention, a hydrocarbon charge stock is contacted with the catalyst in a hydrocarbon conversion zone. This contacting may be accomplished by using the catalyst in a fixed-bed system, a moving-bed system, a fluidized-bed system, or in a batch-type operation. The hydrocarbon charge stock and, if desired, a hydrogen-rich gas as diluent are typically preheated by any suitable heating means to the desired reaction temperature and then are passed into a conversion zone containing the catalyst of the invention. It is, of course, understood that the conversion zone may be one or more separate reactors with suitable means therebetween to ensure that the desired conversion temperature is maintained at the entrance to each reactor. It is also important to know that the reactants may be contacted with the catalyst bed in either upward, downward, or radial-flow fashion with the latter being preferred. In addition, the reactants may be in the liquid phase, a mixed liquid-vapor phase, or a vapor phase when they contact the catalyst. Best results are obtained when the reactants are in the vapor phase.

As indicated heretofore, the catalyst may be utilized within the reaction zone as a fixed-bed system, a moving-bed system, a fluidized-bed system, or in a batch-type operation; however, in view of the operational advantages well recognized in the art, it is preferred to utilize the catalyst of the present invention in a moving-bed system. In such a system, the reaction zone may be one or more separate reactors with heating means therebetween to compensate for the endothermic nature of the dehydrocyclization reaction that takes place in each catalyst bed. The hydrocarbon feedstream, preferably comprising $C_6$–$C_8$ nonaromatic hydrocarbons, is charged to the reaction zone as a continuous moving bed. Therein it is contacted with the hydrocarbon charge stock to effect the dehydrocyclization thereof.

After contact with the catalyst, the hydrocarbon charge stock having undergone dehydrocyclization is withdrawn as an effluent stream from the reaction zone and passed through a cooling means to a separation zone. In the separation zone, the effluent may be separated into various constituents depending upon the desired products. When hydrogen is utilized as a diluent in the reaction zone, the separation zone will typically comprise a vapor-liquid equilibrium separation zone and a fractionation zone. A hydrogen-rich gas is separated from a high octane liquid product containing aromatics generated within the dehydrocyclization zone. After separation, at least a portion of the hydrogen-rich gas may be recycled back to the reaction zone as diluent. The balance of the hydrogen-rich gas may be recovered for use elsewhere. The high octane liquid product comprising aromatics may then be passed to a fractionation zone to separate aromatics from the unconverted constituents of the charge stock. These unconverted constituents may then be passed back to the reaction zone for processing or to other processes for utilization elsewhere.

A wide range of hydrocarbon charge stocks may be employed in the process of the present invention. The exact charge stock utilized will, of course, depend on the precise use of the catalyst. Typically, hydrocarbon charge stocks which may be used in the present invention will contain naphthenes and paraffins, although in some cases, aromatics and olefins may be present. Accordingly, the class of charge stocks which may be utilized includes straight-run naphthas, natural naphthas, synthetic naphthas, and the like. Alternatively, straight-run and cracked naphthas may also be used to advantage. The naphtha charge stock may be a full-boiling range naphtha having an initial boiling point of from about 10°–66° C. and an end boiling point within the range of from about 163°–218° C., or may be a selected fraction thereof. It is preferred that the charge stocks employed in the present invention be treated by conventional catalytic pretreatment methods such as hydrorefining, hydrotreating, hydrodesulfurization, etc., to remove substantially all sulfurous, nitrogenous, and water-yielding contaminants therefrom.

It is preferred that the charge stock of the instant invention substantially comprise paraffins. This, of course, is a result of the fact that the purpose of a dehydrocyclization process is to convert paraffins to aromatics. Because of the value of $C_6$–$C_8$ aromatics, it is additionally preferred that the hydrocarbon charge stock comprise $C_6$–$C_8$ paraffins. However, notwithstanding this preference, the hydrocarbon charge stock may comprise naphthenes, aromatics, and olefins in addition to $C_6$–$C_8$ paraffins.

In order to more fully demonstrate the attendant advantages arising from the present invention, the following examples are set forth. It is to be understood that the following is by way of example only and is not intended as an undue limitation on the otherwise broad scope of the present invention.

It should be understood that there are three parameters useful in evaluating hydrocarbon conversion process and catalyst performance, and in particular in evaluating and comparing dehydrocyclization catalysts. The first is "activity" which is a measure of the catalyst's ability to convert reactants at a specified set of reaction conditions. The second catalyst performance criteria is "selectivity" which is an indication of the catalyst's ability to produce a high yield of the desired product. The third parameter is "stability" which is a measure of the catalyst's ability to maintain its activity and selectivity over time. In the appended examples, the criteria which will be of interest is catalyst selectivity. For purposes of the following, the catalyst of the invention is exemplified as a dehydrocyclization catalyst and the measure of catalyst selectivity is the conversion of the paraffin reactants to aromatics.

BRIEF DESCRIPTION OF THE DRAWING

The drawing graphically illustrates the clear dependency of the aromatics produced, shown as selectivity to aromatics in weight percent, as a function of the measured surface-deposited alkali metal index of the catalyst used. Process Runs A and D, both of the instant invention, yield the highest selectivity to aromatics.

EXAMPLE I

A first catalyst was made in accordance with the invention. Fifty grams of potassium form L-zeolite having an average crystallite size of 275 angstroms were slurried in a solution of 12.8 grams of potassium bicarbonate and 100 cc of deionized water. The potassium/zeolite slurry was evaporated to dryness and then calcined in air at 480° C. for 3 hours. The resulting potassium-impregnated zeolite was then subjected to an ion exchange step in order to composite platinum thereon. This was effected by placing the potassium-impregnated zeolite into 200 cc of a 0.020M. $Pt(NH_3)_4Cl_2$/0.90M. KCl solution. After three days at